United States Patent [19]

Zabotto neé Arribau et al.

[11] Patent Number: 4,637,933
[45] Date of Patent: Jan. 20, 1987

[54] COMPOSITION FOR CLEANING THE SKIN

[75] Inventors: Arlette Zabotto neé Arribau, Paris; Jean-Claude Contamin, Chilly Mazarin; Christian Zaffran, Elancourt; Constantin Koulbanis, Paris, all of France

[73] Assignee: L'Oreal, Paris, France

[21] Appl. No.: 692,625

[22] Filed: Jan. 18, 1985

Related U.S. Application Data

[63] Continuation of Ser. No. 169,767, Jul. 17, 1980, abandoned, which is a continuation of Ser. No. 1,008, Jan. 4, 1979, abandoned.

[30] Foreign Application Priority Data

Jan. 6, 1978 [LU] Luxembourg .......................... 78831

[51] Int. Cl.$^4$ ...................... A61K 33/24; A61K 33/26
[52] U.S. Cl. .................................... 424/131; 424/147; 514/938; 514/949
[58] Field of Search .......................... 514/63, 949, 938; 424/147, 131

[56] References Cited

U.S. PATENT DOCUMENTS 3,981,996 9/1976 Leigh .................................. 424/243

OTHER PUBLICATIONS

Sagarin, Cosmetics Science & Technology, 1952, pp. 166, 167, 1004 & 1005.
English China Clay Salts Co., Ltd. (ECC) Technical Pub. Jul., 1975.

*Primary Examiner*—Leonard Schenkman
*Attorney, Agent, or Firm*—Cushman, Darby & Cushman

[57] ABSTRACT

A cosmetic composition based on an oil-in-water emulsion containing an oil phase, a water phase, an emulsifying agent, and a mineral phase which contains, for instance, a clay, is disclosed.

4 Claims, No Drawings

COMPOSITION FOR CLEANING THE SKIN

This is a continuation of application Ser. No. 169,767, filed July 17, 1980, which is a continuation of Ser. No. 001,008, filed Jan. 4, 1979, both abandoned.

The present invention has for an object a new cosmetic composition for cleaning the skin which is in the form of an oil-in-water emulsion which contains a mineral phase.

At this point in time, many types of compositions for cleaning the skin, and notably for removing makeup, exist; these compositions can take many diverse forms, and often are in the form of creams or milks.

The object of these compositions is to eliminate, in an efficacious manner, impurities which are soluble in oils and soluble in water.

The aforementioned impurities consist principally of residues of makeup which contain pigments, pollutants from the atmosphere and grease resulting from excessive sebum or from products of a makeup.

The compositions utilized up until now when characterized by good cleansing action have been characterized by a major disadvantage of provoking the elimination of complex lipids of the skin which leads ultimately to discomfort, characterized by stinging due to drying of the skin.

The present invention provides a remedy for those different disadvantages and inconveniences and provides compositions of the "wash off cream" type in the form of an oil-in-water emulsion for cleansing the skin and for removing makeup by applying the composition to the face or to the body and then removing it by washing with water.

In this manner, excellent cleansing results with removal of all impurities and pollutants, without imparting a disagreeable appearance of dryness to the skin, but rather providing a sensation of softness and suppleness of the skin.

The results, according to the invention, are obtained thanks to the presence of a mineral phase essentially constituted of a clay of the kaolinite type of a composition having determined characteristics.

Indeed, this mineral phase, by its absorbing power, removes impurities from the skin without provoking skin irritation.

An object of the present invention is an industrial product, a new cosmetic composition for cleansing the skin, and, in particular, for removing makeup, which takes the form of an oil-in-water emulsion containing an oil phase, a water phase, and an emulsifying agent and a mineral phase, said mineral phase being essentially constituted of a clay of the kaolinite type in the form of particles having a size of less than 60 microns, 25% by weight, preferably 15% by weight, of the particles, having an average diameter of more than two microns, said clay having a quartz content of less than 20% by weight, and preferably less than 10%, and a thixotrophy less than or equal to 6.

The clay of the koalinite type used in compositions of the invention ought to include a percentage of kaolinite greater than 50%, and preferably greater than 60% by weight.

Moreover, the silica content of the clay ought to be preferably less than 60% while its aluminum content is greater than or equal to 28%.

After undertaking numerous comparative attempts, it has been established that it is necessary to utilize clays of the kaolinite type having the foregoing characteristics in order to realize the excellent results of the subject invention.

Indeed, it has been established that in utilizing other types of clays which do not provide the characteristics mentioned above, of particle size, quartz content and thixotrophy, cosmetic compositions presenting all of the qualities required for cleaning the skin and permitting the cleansed skin to be soft and supple cannot be obtained.

In a cleansing composition, according to the invention, the clay content of the kaolinite type is from 1% to 30%, particularly from 1 to 12%, and preferably from 3 to 8% by weight, of the total composition.

Clays of the kaolinite type characterized by the above-mentioned characteristics and used in the invention, include those sold by English China Clay International under the trade denominations:

(1) "HYWITE SUPERB"-a kaolinite type clay having (i) the following chemical analysis: $SiO_2$—49%; $Al_2O_3$—32%; $Fe_2O_3$—1.0%; $TiO_2$—0.9%; $MgO$—0.4%; $CaO$—0.2%; $K_2O$—2.1%; $Na_2O$—0.2% and L.O.I—13.5%; (ii) the following mineralogical composition: 68% kaolinite; 20% micaceous material; 7% quartz; and 4% carbonaceous material; and (iii) the following particle size distribution: 3.0%>53 $\mu$m; 5%>5 $\mu$m; 87%<1 $\mu$m; and 73%<0.5 $\mu$m;

(2) "HYWITE TITAN"-a kaolinite type clay having (i) the following chemical analysis: $SiO_2$—45%; $Al_2O_3$—31%; $Fe_2O_3$—1.1%; $TiO_2$—0.9%; $MgO$—0.4%; $CaO$—0.4%; $K_2O$—2.4%; $Na_2O$—0.3% and L.O.I.—18.4%; (ii) the following mineralogical composition: 60% kaolinite; 22% micaceous material; 4% quartz; and 12% carbonaceous material; and (iii) the following particle size distribution: 7.0%>53 $\mu$m; 10%>5 $\mu$m; 86%<1 $\mu$m; and 70%<0.5 $\mu$m;

(3) "HYWITE ATLAS"-a kaolinite type clay having (i) the following chemical analysis: $SiO_2$—46%; $Al_2O_3$—31%; $Fe_2O_3$—1.1%; $TiO_2$—0.9%; $MgO$—0.3%; $CaO$—0.3%; $K_2O$—2.0%; $Na_2O$—0.2% and L.O.I.—18.0%; (ii) the following mineralogical composition: 66% kaolinite; 18% micaceous material, 6% quartz; and 9% carbonaceous material; and (iii) the following particle size distribution: 5.0%>53 $\mu$m; 7%>5 $\mu$m; 86%<1 $\mu$m; and 70%<0.5 $\mu$m;

(4) "HYMOD ROC"-a kaolinite type clay having (i) the following chemical analysis: $SiO_2$—57%; $Al_2O_3$—28%; $Fe_2O_3$—1.5%; $TiO_2$—1.1%; $MgO$—0.5%; $CaO$—0.2%; $K_2O$—3.0%; $Na_2O$—0.4% and L.O.I.—8.0%; (ii) the following mineralogical composition: 52% kaolinite; 31% micaceous material; 15% quartz; and trace carbonaceous material; and (iii) the following particle size distribution: 0.5%>53 $\mu$m; 4%>5 $\mu$m; 82%<1 $\mu$m; and 74%<0.5 $\mu$m;

(5) "HYCAST Al"-a kaolinite type clay having (i) the following chemical analysis: $SiO_2$—55%; $Al_2O_3$—30%; $Fe_2O_3$—1.38%; $TiO_2$—1.0%; $MgO$—0.4%; $CaO$—0.3%; $K_2O$—2.8%; $Na_2O$—0.3% and L.O.I.—9.0% (ii) the following mineralogical composition: 58% kaolinite; 28% micaceous material; 13% quartz; and a trace of carbonaceous material; and (iii) the following particle size distribution: 2%>53 $\mu$m; 7%>5 $\mu$m; 78%<1 $\mu$m; and 67%<0.5 $\mu$m;

(6) "HYWITE ALUM"-a kaolinite type clay having (i) the following chemical analysis: $SiO_2$—42%; $Al_2O_3$—31%; $Fe_2O_3$—1.4%; $TiO_2$—0.7%; $MgO$—0.2%; $CaO$—0.2%; $K_2O$—1.0%; $Na_2O$—0.1% and L.O.I.—23.0%; (ii) the following mineralogical composition:

77% Kaolinite; 8% micaceous material; 2% quartz; and 12% carbonaceous material; and (iii) the following particle size distribution: 4.6%>53 μm; 5%>5 μm; 78%<1 μm; and 60%<0.5 μm;

(7) "HYMOD EXCELSIOR"-a kaolinite type clay having (i) the following chemical analysis: $SiO_2$—48%; $Al_2O_3$—35%; $Fe_2O_3$—1.6%; $TiO_2$—1.1%; MgO—0.3%; CaO—0.3%; $K_2O$—1.2%; $Na_2O$—0.2% and L.O.I.—12.0%; (ii) the following mineralogical composition: 83% kaolinite; 11% micaceous material; 4% quartz; and 1% carbonaceous material; and (iii) the following particle size distribution: 0.6%>53 μm; 3%>5 μm; 85%<1 μm; and 80%<0.5 μm;

(8) "HYMOD PRIMA"-a kaolinite type clay having (i) the following chemical analysis: $SiO_2$—54%; $Al_2O_3$—30%; $Fe_2O_3$—1.3%; $TiO_2$—1.6%; MgO—0.5%; CaO—0.3%; $K_2O$—2.8%; $Na_2O$—0.4% and L.O.I.—9.0%; (ii) the following mineralogical composition: 59% kaolinite; 27% micaceous material; 12% quartz and trace of cabonaceous material; and (iii) the following particle size distribution: 0.2%>53 μm; 5%>5 μm; 83%<1 μm; and 73%<0.5 μm;

(9) "HYMOD BLUE"-a kaolinite type clay having (i) the following chemical analysis: $SiO_2$—52%; $Al_2O_3$—31%; $Fe_2O_3$—1.5%; $TiO_2$—0.9%; MgO—0.5%; CaO—0.3%; $K_2O$—3.1%; $Na_2O$—0.4% and L.O.I.—9.5%; (ii) the following mineralogical composition: 57% kaolinite; 33% micaceous material; 8% quartz; and 1% carbonaceous material; and (iii) the following particle size distribution: 0.3%>53 μm; 4%>5 μm; 79%<1 μm; and 62%<0.5 μm; and

(10) "KAOLIN SUPREME"-a kaolinite type clay having (i) the following chemical analysis: $SiO_2$—46.6%; $Al_2O_3$—38.3%; $Fe_2O_3$—0.49%; $TiO_2$—0.05%; CaO—0.2%; MgO—0.2%; $K_2O$—0.68%; $Na_2O$—0.07% and L.O.I.—13.4%; (ii) the following mineralogical composition: greater than 50% kaolinite and quartz less than 20%; and (iii) the following particle size distribution: 0.2%>10 μm and 94%<2 μm.

According to a particular embodiment of the invention, the mineral phase can also contain montmorillonite. In this case, the composition contains 0.1 to 10%, preferably 0.5 to 5% by weight of the compound of the total composition.

It has been established that by addition of the montmorillonite to the mineral phase, it is possible to increase, in a surprising manner, the softness and suppleness of the skin.

The proportion of the emulsifying agent in the compositions according to the invention is generally from 1 to 20%, and preferably from 2 to 12%.

Different emulsifying agents which can be used in the emulsions according to the invention, include:

polyoxyethylenated or polyglycerolated esters of fatty acids;

oxyethylenated or polyglycerolated fatty alcohols, as, for example, oleic acid polyoxyethylenated with 10 moles of ethylene oxide, stearyl alcohol polyoxyethylenated with 10 to 15 or 20 moles of ethylene oxide, oleic alcohol polyglycerolated with 4 moles of glycerol and snythetic fatty alcohols containing 9 to 15 carbon atoms polyoxyethylenated with 5 or 10 moles of ethylene oxide;

alkyl sulfates oxyethylenated or not, such as sodium lauryl sulfate, ammonium lauryl sulfate, sodium cetyl stearyl sulfate, cetyl stearyl sulfate of triethanolamine, lauryl sulfate of monoethanolamine, lauryl ether sulfate of sodium which is oxyethylenated (with, for example, 2.2 moles of ethylene oxide) and the lauryl ether sulfate of monoethanolamine which is oxyethylenated (with e.g. 2.2 moles of ethylene oxide)

and soaps, such as the stearate of triethanolamine.

According to the invention, the aqueous phase of the emulsions comprises from 30 to 90%, and preferably from 50 to 80%, by weight of the total weight of the composition.

The aqueous phase of the emulsions can contain gelifiers, such as hydroxy propyl methyl cellulose ("METHOCEL F4 M" sold by DOW), aliginates such as those sold under the commercial denomination of "AUBY GUM $X_2$" by Pierrefite Auby, and the like.

The oil of the oil phase comprises from 5 to 40%, and preferably from 10 to 20% by weight of the total weight of the composition. The oil phase can be a mixture of at least one oil and at least one wax, and in this embodiment will comprise 5 to 40%, preferably 10 to 20% by weight of the composition.

According to the invention, the oil phase of the emulsions can be prepared from a large variety of products such as:

hydrocarbon oils, such as paraffin oil, viscous vaseline, perhydrosqualene, solutions of micro-crystalline waxes in paraffin oil and purcellin oil.

animal or vegetable oils such as horse oil, pork fat, oil of almond, oil of calophyllum, olive oil, and avocado oil.

saturated esters (which will not become rancid) and which are good penetrating agents such as isopropyl palmitate, isopropyl myristate, isooctyl myristate, or isodecyl myristate, ethyl palmitate, isopropyl adipate, and the triglycerides of octanoic acid and of decanoic acid.

There can also be added to the oil phase silicone oils such as dimethylpolysiloxane and methylphenylpolysiloxane, which are soluble in other oils. Further, the oil phase can also contain phenylethyl alcohol.

The oil phase can additionally contain such waxes as carnauba wax, candellila wax, beeswax, microcrystalline waxes and ozokerite.

As adjuvants of the oil phase, there can equally be used long chain fatty alcohols, such as a fatty alcohol of beeswax, copra alcohol, myristic alcohol, cetyl alcohol, stearyl alcohol, and hydroxy stearic alcohol.

The cosmetic compositions according to the invention lend themselves preferably to a cream form or a milk form and can be applied to the face and/or to the whole body.

The cosmetic compositions according to the invention can equally contain all the ingredients generally used in cosmetics and, particularly, anionic wetting agents; non-ionic, cationic or amphoteric wetting agents; perfumes; preservative agents, such as methyl parahydroxybenzoate or propyl parahydroxybenzoate, these latter permitting increase of the stability and the longevity of the emulsions.

The present invention also has for an object a process for preparing the oil-in-water emulsions, which are described above.

The process of preparing the oil-in-water emulsions essentially includes dispersing in the aqueous phase, optionally containing the preservative agent, the mineral phase, at a temperature of about 80° C.; then adding thereto an emulsifying agent; and then adding the oil phase previously heated to a temperature of about 80° C. to the water phase maintained at the same temperature, and admixing with agitation.

After cooling to a temperature of about 40° C., perfume can be added with agitation and the emulsion is then cooled to about 25° C.

The following examples of compositions are set forth with a view of improving the understanding of the invention, by way of illustration, but not by way of limitation.

COMPOSITIONS

Example 1

In accordance with the invention, an oil-in-water emulsion for cleaning the face is prepared by proceeding with the mixture of the following ingredients:

| | |
|---|---|
| Mineral oil (paraffin oil) | 10 g |
| Stearyl ether polyoxyethylenated with 10 moles of ethylene oxide | 2 g |
| Cetyl ether polyoxyethylenated with 10 moles of ethylene oxide | 2 g |
| Glycerine monostearate | 4 g |
| Cetyl alcohol | 1 g |
| Stearyl alcohol | 1 g |
| Hydroxy-propyl methyl cellulose (Methocel F4M, sold by DOW) | 0.3 g |
| 2-"Cocoyl"-1-"sodium carboxy methyl"-1-[2-(sodium carboxy methoxy)ethyl]-2-imadozolinium hydroxyde (Miranol C2M) | 2 g |
| Methyl parahydroxybenzoate | 0.2 g |
| Clay of the Kaolinite type, "Hycast Al" | 5 g |
| Perfume | 0.5 g |
| Demineralized water, q.s.p. | 100 g |

By application of this composition to the face, with the aid of light massage, after rinsing with water or with the aid of a set cloth, a perfect cleansing results while leaving the skin soft and supple.

Example 2

According to the invention, an oil-in-water emulsion for cleansing the body is prepared by proceeding with a mixture of the following ingredients:

| | |
|---|---|
| Glycerol monostearate | 1 g |
| Cetyl alcohol | 2.5 g |
| Isopropyl myristate | 5 g |
| Mixture of ceto-stearyl alcohol and of oxyethylenated fatty alcohols ("Sinnowax AO" sold by HENKEL, of France) | 3.5 g |
| Clay of the Kaolinite type "Hywite Superb" | 1 g |
| Propyl parahydroxy benzoate | 0.3 g |
| Alkyl amide betaine of fatty acids containing 12-18 carbon atoms sold under the trade denomination of "Tego Betaine L7" sold by Goldschmidtt | 1 g |
| Perfume | 0.5 g |
| Demineralized water, q.s.p. | 100 g |

By application of this composition to the body while effectuating light massage, and by then rinsing with water, an excellent cleansing of the skin of the body results while it is established that the skin is supple and lithsome.

Example 3

According to the invention an oil-in-water emulsion for cleansing the skin and the body is prepared by proceeding with a mixture of the following ingredients:

| | |
|---|---|
| Mineral oil (paraffin oil) | 7 g |
| Palmitate of glyceryl ethyl-2 hexyl ether | 3 g |
| Stearyl ether polyoxyethylenated with the aid of 10 moles of ethylene oxide | 2 g |
| Cetyl ether polyoxyethylenated with the aid of 10 moles of ethylene oxide | 2 g |
| Glycerine monostearate | 4 g |
| Cetyl alcohol | 1 g |
| Stearyl alcohol | 1 g |
| Hydroxy-propyl methyl cellulose | 0.3 g |
| "Miranol $C_2$ M" (as in Example 1) | 2 g |
| Propyl parahydroxybenzoate | 0.15 g |
| Clay of Kaolinite type "Kaolin Supreme" | 3 g |
| Perfume | 0.4 g |
| Demineralized water, q.s.p. | 100 g |

By application of this composition to the body followed by rinsing with water, it is established that the skin is clean, supple and soft.

The clays of the kaolinite type used in the above examples are more particularly identified as follows:

"Hycast Al" has the following chemical analysis: $SiO_2$—55%; $Al_2O_3$—30%; $Fe_2O_3$—1.3%; $TiO_2$—1.0%; $MgO$—0.4%; $CaO$—0.3%; $K_2O$—2.8%; $Na_2O$—0.3%; L.O.I.—9.0%. Its mineralogical composition is as follows: 58% kaolinite; 28% micaceous material; 13% quartz; and a trace of carbonaceous material. It has the following particle size distribution: 2% > 53 μm; 7% > 5 μm; 78% > 1 μm and 67% > 0.5 μm.

"Hywite Superb" has the following chemical analysis: $SiO_2$—49%, $Al_2O_3$—32%; $Fe_2O_3$—1.0%; $MgO$—0.4%; $CaO$—0.2%; $K_2O$—2.1%; $Na_2O$—0.2% and L.O.I.—13.5%. Its mineralogical composition is as follows: 68% kaolinite; 20% micaceous material; 7% quartz; and 4% carbonaceous material. It has the following particle size distribution: 3.0% > 53 μm; 5% > 5 μm; 87% > 1 μm; and 73% > 0.5 μm.

"Kaolin Supreme" has the following chemical analysis: $SiO_2$—46.6%; $Al_2O_3$—38.3%; $Fe_2O_3$—0.49%; $TiO_2$—0.05%; $CaO$—0.2%; $MgO$—0.2%; $K_2O$—0.68%; $Na_2O$—0.07%; and L.O.I.—13.43%. It has the following particle size distribution: 0.2% > 10 μm and 94% < 2 μm.

What is claimed is:

1. A cosmetic composition for cleansing the skin, in the form of an oil-in-water emulsion, consisting essentially of 5-30 percent by weight, based on the total weight of the composition, of an oil phase; 30 to 90 percent by weight, based on the total weight of the composition, of a water phase; 1 to 20 percent by weight, based on the total weight of the composition, of an emulsifying agent; and 1 to 30 percent by weight, based on the total weight of the composition, of a mineral phase; said mineral phase being a clay of the kaolinite type in the form of particles having a particle size of less than 60 microns wherein less than 15 percent by weight of said particles have a size which is greater than 2 microns, said clay having a quartz content of less than 20 percent, a kaolinite content greater than 50 percent and a thixotropy less than or equal to 6.

2. A cosmetic composition for cleansing the skin in the form of an oil-in-water emulsion, comprising an oil phase, a water phase, an emulsifying agent and a mineral phase, said mineral phase being a clay of the kaolinite type selected from the group consisting of (1) a kaolinite type clay having (i) the following chemical analysis: $SiO_2$—49%; $Al_2O_3$—32%; $Fe_2O_3$—1.0%; $TiO_2$—0.9%; MgO—0.4%; CaO—0.2%; $K_2O$—2.1%; $Na_2O$—0.2% and L.O.I.—13.5%; (ii) the following mineralogical composition: 68% kaolinite; 20% micaceous material; 7% quartz; and 4% carbonaceous material; and (iii) the following particle size distribution: 3.0% > 53 μm; 5% > 5 μm; 87% < 1 μm; and 73% > 0.5 μm;

(2) a kaolinite type clay having (i) the following chemical analysis: $SiO_2$—45%; $Al_2O_3$—31%; $Fe_2O_3$—1.1%; $TiO_2$—0.9%; MgO—0.4%; CaO—0.4%; $K_2O$—2.4%; $Na_2O$—0.3% and L.O.I.—18.4%; (ii) the following mineralogical composition: 60% kaolinite; 22% micaceous material; 4% quartz; and 12% carbonaceous material; and (iii) the following particle size distribution: 7.0% > 53 μm; 10% > 5 μm; 86% < 1 μm; and 70% < 0.5 μm;

(3) a kaolinite type clay having (i) the following chemical analysis: $SiO_2$—46%; $Al_2O_3$—31%; $Fe_2O_3$—1.1%; $TiO_2$—0.9%; MgO—0.3%; CaO—0.3%; $K_2O$—2.0%; $Na_2O$—0.2% and L.O.I.—18.0%; (ii) the following mineralogical composition: 66% kaolinite; 18% micaceous material, 6% quartz; and 9% carbonaceous material; and (iii) the following particle size distribution: 5.0% > 53 μm; 7% > 5 μm; 86% < 1 μm; and 70% < 0.5 μm;

(4) a kaolinite type clay having (i) the following chemical analysis: $SiO_2$—57%; $Al_2O_3$—28%; $Fe_2O_3$—1.5%; $TiO_2$—1.1%; MgO—0.5%; CaO—0.2%; $K_2O$—3.0%; $Na_2O$—0.4% and L.O.I.—8.0%; (ii) the following mineralogical composition: 52% kaolinite; 31% micaceous material; 15% quartz; and trace carbonaceous material; and (iii) the following particle size distribution: 0.5% > 53 μm; 4% > 5 μm; 82% < 1 μm; and 74% < 0.5 μm;

(5) a kaolinite type clay having (i) the following chemical analysis: $SiO_2$—55%; $Al_2O_3$—30%; $Fe_2O_3$—1.38%; $TiO_2$—1.0%; MgO—0.4%; CaO—0.3%; $K_2O$—2.8%; $Na_2O$—0.3% and L.O.I.—9.0% (ii) the following mineralogical composition: 58% kaolinite; 28% micaceous material; 13% quartz; and a trace of carbonaceous material; and (iii) the following particle size distribution: 2% > 53 μm; 7% > 5 μm; 78% < 1 μm; and 67% < 0.5 μm;

(6) a kaolinite type clay having (i) the following chemical analysis: $SiO_2$—42%; $Al_2O_3$—31%; $Fe_2O_3$—1.4%; $TiO_2$—0.7%; MgO—0.2%; CaO—0.2%; $K_2O$—1.0%; $Na_2O$—0.1% and L.O.I.—23.0%; (ii) the following mineralogical composition: 77% kaolinite; 8% micaceous material; 2% quartz; and 12% carbonaceous material; and (iii) the following particle size distribution: 4.6% > 53 μm; 5% > 5 μm; 78% < 1 μm; and 60% < 0.5 μm;

(7) a kaolinite type clay having (i) the following chemical analysis: $SiO_2$—48%; $Al_2O_3$—35%; $Fe_2O_3$—1.6%; $TiO_2$—1.1%; MgO—0.3%; CaO—0.3%; $K_2O$—1.2%; $Na_2O$—0.2% and L.O.I.—12.0%; (ii) the following mineralogical composition: 83% kaolinite; 11% micaceous material; 4% quartz; and 1% carbonaceous material; and (iii) the following particle size distribution: 0.6% > 53 μm; 3% > 5 μm; 85% < 1 μm; and 80% < 0.5 μm;

(8) a kaolinite type clay having (i) the following chemical analysis: $SiO_2$—54%; $Al_2O_3$—30%; $Fe_2O_3$—1.3%; $TiO_2$—1.6%; MgO—0.5%; CaO—0.3%; $K_2O$—2.8%; $Na_2O$—0.4%; and L.O.I.—9.0%; (ii) the following mineralogical composition: 59% kaolinite; 27% micaceous material; 12% quartz and trace of cabonaceous material; and (iii) the following particle size distribution: 0.2% > 53 μm 5% > 5 μm; 83% < 1 μm; and 73% < 0.5 μm;

(9) a kaolinite type clay having (i) the following chemical analysis: $SiO_2$—52%; $Al_2O_3$—31%; $Fe_2O_3$—1.5%; $TiO_2$—0.9%; MgO—0.5%; CaO—0.3%; $K_2O$—3.1%; $Na_2O$—0.4% and L.O.I.—9.5%; (ii) the following mineralogical composition: 57% kaolinite; 33% micaceous material; 8% quartz; and 1% carbonaceous material; and (iii) the following particle size distribution: 0.3% > 53 μm; 4% > 5 μm; 79% < 1 μm; and 62% < 0.5 μm, said kaolinite type clays having a thixotropy less than or equal to 6.

3. A cosmetic composition for cleansing the skin in the form of an oil-in-water emulsion, comprising an oil phase, a water phase, an emulsifying agent and a mineral phase, said mineral phase being a clay of the kaolinite type having (1) the following chemical analysis: $SiO_2$—55%; $Al_2O_3$—30%; $Fe_2O_3$—1.38%; $TiO_2$—1.0%; MgO—0.4%; CaO—0.3%; $K_2O$—2.8%; $Na_2O$—0.3% and L.O.I.—9.0%; (2) the following mineralogical composition: 58% kaolinite; 28% micaceous material; 13% quartz; and a trace of carbonaceous material; (3) the following particle size distribution: 2% > 53 μm; 7% > 5 μm; 78% < 1 μm and 67% < 0.5 μm and (4) a thixotropy less than or equal to 6.

4. A cosmetic composition for cleansing the skin in the form of an oil-in-water emulsion, comprising an oil phase, a water phase, an emulsifying agent and a mineral phase, said mineral phase being a kaolinite type clay having (i) the following chemical analysis: $SiO_2$—46.6%; $Al_2O_3$—38.3%; $Fe_2O_3$—0.49%; $TiO_2$—0.05%; CaO—0.2%; MgO—0.2%; $K_2O$—0.68%; $Na_2O$—0.07% and L.O.I.—13.4%; (ii) the following mineralogical composition: greater than 50% kaolinite and quartz less than 20%; and (iii) the following particle size distribution: 0.2% > 10 μm; and 94% < 2 μm; said clay having a thixotropy less than or equal to 6.

* * * * *